United States Patent [19]

Kulla

[11] Patent Number: 5,348,884
[45] Date of Patent: Sep. 20, 1994

[54] DEVICE AND METHOD FOR THE DETECTION OF MICROORGANISMS WHICH PRODUCE LOW-MOLECULAR-WEIGHT METABOLITES

[75] Inventor: Hans Kulla, Visperterminen, Switzerland

[73] Assignee: Lonza Ltd., Basel, Switzerland

[21] Appl. No.: 101,931

[22] Filed: Aug. 4, 1993

Related U.S. Application Data

[62] Division of Ser. No. 781,023, Oct. 18, 1991.

[30] Foreign Application Priority Data

Oct. 23, 1990 [CH] Switzerland ............... 3391/90

[51] Int. Cl.$^5$ .............. C12M 1/34; C12M 1/00; C12N 11/00; C12Q 1/02
[52] U.S. Cl. .......................... 435/291; 435/4; 435/29; 435/35; 435/287; 435/297; 435/299; 435/301; 435/311; 435/807; 73/23.2; 73/29.01; 73/29.04; 73/64.54
[58] Field of Search ............. 435/34, 35, 36, 287, 435/297, 4, 29, 291, 299, 301, 311, 807; 73/23.2, 29.01, 29.04, 64.54

[56] References Cited

U.S. PATENT DOCUMENTS

3,929,582  12/1975  Kellner ................ 435/3
4,421,849  12/1983  Breuker ............... 435/32

FOREIGN PATENT DOCUMENTS

0124285  11/1984  European Pat. Off. .

OTHER PUBLICATIONS

Ullmann's Encyclopedia of Industrial Chemistry, 5th Ed., vol. B3, VCH Verlagsgesellschaft mbH, 1988, pp. 9-8 and 9-9.
Austin "Shreve's Chemical Process Industries", Fifth Edition, McGraw Hill Book Company.
Lim et al., Applied and Environmental Microbiology, Feb. 1977, pp. 328-333 vol. 33, No. 2.
Patent Abstracts of Japan, vol. 9, No. 309, Dec. 5, 1985.
T. A. McMeekin et al., "Detection of Volatile Sulfide—Producing Bacteria Isolated From Poultry-Processing Plants", Applied and Environmental Microbiology, vol. 35, No. 6, Jun. 1978.

(List continued on next page.)

*Primary Examiner*—Michael G. Wityshyn
*Assistant Examiner*—Jane Williams
*Attorney, Agent, or Firm*—Brumbaugh, Graves, Donohue & Raymond

[57] ABSTRACT

Selective detection of microorganisms is achieved by a screening technique in which radioactively labeled, low-molecular-weight metabolites produced by microorganisms to be detected reach an adsorption medium through a semipermeable medium which passes the labeled metabolites but blocks the labeled incubation medium. The adsorption medium is then subject to analysis, such as autoradiography, to detect the presence of the labeled metabolites. An analytical assembly for such detection includes a filter membrane support for growing microorganisms in discrete colonies and for holding a radioactively labeled incubating medium applied thereon, a semipermeable filter medium covering the support having the grown microorganisms and the incubating medium for passing low-molecular-weight, labeled metabolites produced by microorganisms of interest while blocking the incubating medium, and a cohesive layer of an adsorption medium conformably disposed with the filter membrane support and the semipermeable medium and being capable of adsorbing the labeled metabolites which have traversed the semipermeable medium during incubation of the assembly. Following incubation of the assembly, the adsorption medium layer is transferable for analysis, e.g., by autoradiography, to detect the presence of labeled metabolites produced by microorganisms of interest and to identify specific colonies of the microorganisms producing the radioactively labeled metabolite.

7 Claims, 1 Drawing Sheet

OTHER PUBLICATIONS

J. L. Firmin et al., "The Biochemical Pathway for the Breakdown of Methyl Cyanide (Acetonitrile) in Bacteria," Biochemical Journal, vol. 158 (1976), pp. 223–229.

B. R. Bochner et al., "Sensitive Fluorographic Detection of $^3H$ and $^{14}C$ on Chromatograms Using Methyl Anthranilate as a Scintillant," Anal. Biochem., vol. 131 (1984), pp. 510–515.

R. A. Laskey, "Radioisotope Detection by Fluorography and Intensifying Screens", Amersham, United Kingdom, Review 23, 1984.

H. Kulla et al., "Interference of Aromatic Sulfo Groups in the Microbial Degradation of the Azo Dyes Orange I and Orange II," Arch. Microbiol., vol. 135 (1983), pp. 1–7.

DEVICE AND METHOD FOR THE DETECTION OF MICROORGANISMS WHICH PRODUCE LOW-MOLECULAR-WEIGHT METABOLITES

This application is a division of application Ser. No. 07/781,023, filed on Oct. 18, 1991.

BACKGROUND OF THE INVENTION

This invention relates to analytical devices and methods for the detection of microorganisms which produce low-molecular-weight metabolites.

As disclosed by J. L. Firmin et al., "The Biochemical Pathway for the Breakdown of Methyl Cyanide (Acetonitrile) in Bacteria" Biochemical Journal., Vol 158 (1976), pp. 223–229, it is known that metabolites formed in a microbiological or biochemical process can be detected as follows: a radioactively labeled substance is admixed to a cell suspension; the mixture is incubated for a certain time; the cells are removed; and a radioactively labeled metabolite is detected, e.g., by liquid-phase scintillation measurement. This widely used detection method is complicated and time consuming. Moreover, as radioactively labeled metabolites are detected independent of their molecular weight, this method is unsuited for the selective detection of microorganisms with specific metabolic performance.

Disclosed in published European patent application, EP-A 124 285, is a detection method for microorganisms in medical test samples. This method, too, suffers from the drawback of registering the totality of radioactively labeled metabolites, making it unsuited as a method for screening metabolites produced by specific microorganisms.

SUMMARY OF THE INVENTION

The invention provides for detection of microorganisms on the basis of their ability to produce a low-molecular-weight metabolite. In accordance with the invention, microorganisms grown on a support, such as a filter membrane, are provided with an incubating medium containing a radioactively labeled substance which can be metabolized into a low-molecular-weight metabolite by the microorganisms. A semipermeable medium is provided to cover the support having the grown microorganisms and the incubating medium. An adsorption medium is positioned adjacent the semipermeable medium so as to be exposed to material passing through the semipermeable medium. The semipermeable medium is selected to be permeable to the low-molecular-weight metabolite but not to the labeled substance in the incubation medium. The adsorption medium is selected to be able to adsorb the low-molecular-weight metabolite. The assembly comprising the support having the microorganisms and the incubation medium, the semipermeable medium and the adsorption medium is incubated for a time sufficient to allow production of a detectable amount of low-molecular-weight metabolite if microorganisms of interest are present, and the adsorption medium is analyzed, e.g., by autoradiography, for the presence of a labeled metabolite. Preferably, the adsorption medium is in the form of a cohesive layer that can transferred to an autoradiography film to allow identification of specific colonies of microorganisms producing the labeled metabolite.

DETAILED DESCRIPTION OF PREFERRED EMBODIMENTS

Figure 1:
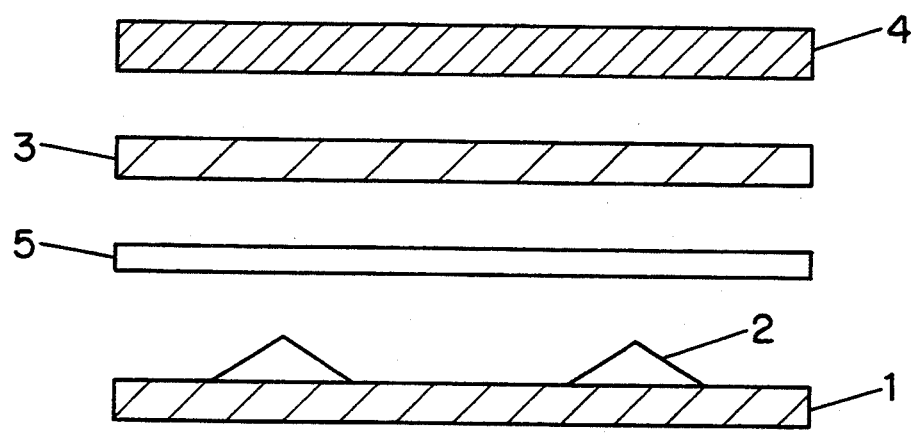
FIG. 1 is a schematic, exploded cross section of a device assembly in accordance with a preferred embodiment of the invention.

In accordance with the invention, microorganisms are selectively detected via the detection of low-molecular-weight metabolites formed in a microbiological process, a radioactively labeled substance being metabolized by microorganisms to produce a radioactively labeled metabolite, and such metabolite being detected by a determination of radioactivity. This technique is advantageously applied to the detection of metabolites whose molecular weight does not exceed approximately 500, and is particularly effective for the detection of metabolites whose molecular weight does not exceed approximately 250.

Among suitable radioactive labeling materials are the isotopes $^{14}C$, $^{3}H$, $^{35}S$, and $^{32}P$. Other biologically suitable radioactive isotopes may be used. Preferred among the above-mentioned isotopes are $^{3}H$ and $^{14}C$. Typically, the specific radioactivity of a radioactively labeled substance is approximately in the range of 1 millicurie/millimole to 20 curie/millimole.

Conveniently, when a substance which is radioactively labeled with $^{3}H$ or $^{14}C$ is metabolized by microorganisms, a low-molecular-weight metabolite is formed which is respectively labeled with either $^{3}H$ or $^{14}C$. Thus, for $^{3}H$ or products labeled with $^{14}C$ such as carbon dioxide, ethanol, lactic acid, acetic acid, formic acid, acetone, butanol, butanediol, acetoine or other metabolites. Of particular importance are substances labeled with $^{3}H$ which are metabolized into $^{3}H_2O$ and substances labeled with $^{14}C$ which are metabolized into $^{14}CO_2$. Radioactively labeled metabolites can be detected by conventional methods, e.g., autoradiography or liquid-phase scintillation measurement. The use of autoradiography is preferred.

An exemplary detection method in accordance with the invention may be illustrated with reference to FIG. 1. Shown in FIG. 1 are the principal components of an assembly comprising a support 1 (e.g., a known filter membrane such as a cellulose filter) on which colonies 2 of microorganisms are grown, a semipermeable filter 3 permeable to metabolites of the microorganisms which are of interest, and an adsorption medium 4.

Conveniently, for the growth of colonies 2, the support 1 is placed on a standard agar medium, e.g., plate-count agar, available from Difco Laboratories, USA. When the microorganism colonies 2 have reached a diameter of approximately 0.1 to 5 millimeters, and preferably 0.5 to 2 millimeters, these colonies are covered with an incubating solution comprising a radioactively labeled substance which can be metabolized by microorganisms of interest to produce a labeled, low-molecular-weight metabolite. To minimize convection in the incubating solution, a viscosity-increasing material may be added, e.g., agar.

Preferably, a hydrophilic sterile filter is used as the support 1, having a pore size of approximately 0.01 to 2 micrometers. For example, such sterile filters may be formed with cellulose nitrate, cellulose acetate, regenerated cellulose, nylon, or some other standard hydrophilic sterile filter material having an appropriate pore size.

The incubating solution may be applied while the support 1 remains on a solid nutrient substrate. Alternatively, it may be advantageous to separate and transfer the support 1 with the microorganism colonies 2 away from the substrate, especially to prevent undue dilution in the detection of $^3H_2O$.

After the microorganisms 2 have been covered with the incubating solution, a semipermeable filter 3 is provided over the support covering the microorganisms 2 and the incubating solution (not shown). The semipermeable filter 3 allows passage of the low-molecular-weight metabolite but not the labeled substance contained in the incubating solution. Preferably, the semipermeable filter 3 is (or has been rendered) hydrophobic. For selective permeability to metabolites, the pore size of the semipermeable filter 3 is advantageously in the range of approximately 0.02 to 2 micrometers and preferably in the range of approximately 0.02 to 0.2 micrometer. Preferably, the semipermeable filter 3 is selected from the following: Goretex ® filters (polytetrafluoroethylene with 0.2- to 0.02-micrometer pore size, disposed on a polyester supporting fabric), glass-fiber filters having appropriate pore sizes and rendered hydrophobic (e.g., by silane treatment), and silicone membranes having appropriate pore sizes and a thickness in the range of approximately 0.1 to 1 millimeter. Alternatively, a semipermeable layer may be made by depositing a hydrophobic powder material, e.g., Aerosil R972 available from Degussa, Germany.

To prevent mixing of the microorganisms of the colonies 2, a supporting fabric 5 may be placed between the support 1 and the semipermeable filter 3. Such a supporting fabric may consist of a net-like cotton fabric, such as gauze. Instead of the support fabric or in addition thereto, another filter membrane, similar to the filter membrane of support 1, for example, may be placed between support 1 and semipermeable filter 3.

An adsorption medium 4 is placed on the semipermeable filter 3 for the adsorption of the low-molecular-weight metabolite passing through the semipermeable filter 3. In the case where $^3H_2O$ is being detected, a glass substrate covered with a molecular sieve or with silica gel is advantageously used as adsorption medium. For the detection of $^{14}CO_2$, a glass substrate covered with lime is preferred. Specifically, a molecular sieve having a pore size in the range of approximately 3 to 4 Angstroms, or, alternatively a silica gel, may be deposited on a glass substrate to a thickness in the range of approximately 0.1 to 5 millimeters. As will be known to those skilled in the art, other adsorbing materials may be used as the adsorption medium, such as gypsum or aluminum oxide.

For added stability of the adsorption medium 4 it may be desirable to use a binder material, e.g., derivatized cellulose, starch, cement, water glass, glass fibers, or any other suitable binder material as is customarily used in the preparation of thin-film chromatography substrates.

The resulting assembly comprising the support 1 with the microorganism colonies 2 and the applied incubating solution (not shown), the supporting fabric 5 (if any), the semipermeable filter 3, and the adsorption medium 4 is incubated for approximately 1 to 12 hours at an appropriate temperature in the range of approximately 5 to 110 degrees C. to allow formation of a detectable amount of labeled,low-molecular-weight metabolite if microorganisms of interest are present. Known incubating media with appropriate radioactive labeling materials may be used. Examples of such incubating media are described hereinbelow. By application of a weight or other compressing means, the thickness of the assembly may be reduced to approximately 5 millimeters, for example. The length of the assembly may be approximately 5 centimeters.

Because the diffusion rate of low-molecular-weight metabolites varies in different semipermeable media, the preferred incubation time depends on the type of semipermeable filter which is being used. When a silicone membrane is used as the semipermeable filter 3, the preferred incubation time is up to approximately 3 hours. In the case where Goretex ® or a hydrophilic glass-fiber filter is used as the semipermeable filter 3, the preferred incubation time is up to approximately 1 hour. The preferred incubation temperature depends on the temperature characteristics of the microorganisms being detected. For example, for the detection of mesophile microorganisms, the preferred incubation temperature is in the range of approximately 30 to 37 degrees C.

After incubation the adsorption medium is removed and may be treated with a suitable scintillator material, such as Enhance ®, available from DuPont, USA. Other suitable scintillator solutions are described by B. R. Bochner et al., Anal. Biochem., Vol. 131 (1984), pp. 510–515.

The invention provides for highly sensitive detection of microorganisms which metabolize a radioactively labeled substance into a metabolite which can be selectively detected in the manner described above. In contrast with known techniques, the microorganism detection technique of the invention is also applicable to colonies of microorganisms grown in large numbers on the surface of a solid nutrient medium.

The technique in accordance with the invention is advantageously used for the detection of microorganisms which produce low-molecular-weight metabolites, and especially for the detection of microorganisms which are capable of converting bound methyl groups into a corresponding alcohol, aldehyde or carbonic acid. For example, the method can be used for the detection of microorganisms capable of oxidizing the labeled methyl groups of 5-methyl-2-chloropyridine into a corresponding acid and labeled water.

In the following examples, the physical quantities described therein are understood to be nominal or approximate.

Example 1. *Alcaligenes eutrophus* (DSM 428) and *Pseudomonas aeruginosa* (DSM 50071) were cultivated separately in a nutrient broth, available from Oxoid, USA, at 30 degrees C., overnight on a shaking machine. Then, one part Pseudomonas culture was mixed with 999 parts Alcaligenes culture, and 0.1 milliliter of this mixture was spread in $10^{-4}$-dilution onto a cellulose nitrate filter, available from Sartorius, USA. The cellulose nitrate filter was placed on plate count agar (PCA), available from Difco, USA. The filter had a diameter of 5 centimeters and a pore size of 0.2 micrometer. Overnight, the cells grew into approximately 1000 colonies with diameters from 0.5 to 1 millimeter. The cellulose nitrate filter supporting the colonies was lifted from the PCA-medium and placed in a Petri dish with the colonies facing up. The filter support with the colonies was soaked with 0.18 milliliter radioactive solution having the following composition: 5 gram/liter melted agar; 5 gram/liter Tryptone, available from Difco, USA; 2.5 gram/liter yeast extract, available from Difco, USA; 2 millimose D-[6-³H(N)]-glucose, at 0.1 curie/millimose, available from NEN/DuPont, USA. Immediately thereafter, a second cellulose filter support, which had been moistened by contact with plate count agar was placed on the colonies, and a hydrophobic TE35-filter (polytetrafluoroethylene on polystyrene available from Schleicher & Schuell, Germany) with a diameter of 8 centimeters and a pore size of 0.2 micrometers was placed on the second cellulose nitrate filter support. Thereafter, a water-specific adsorption plate was immediately deposited with the adsorption layer facing down so as to be exposed to material passing through the TE35-filter. The adsorption plate had been produced as follows: 8 grams of 4-Angstrom molecular sieve powder with grain size from 2 to 3 micrometers was suspended in 7 milliliters of water, and 0.1 gram of glass fiber was then added. The glass fiber consisted of finely ground GF/D-filter (glass-fiber filter, Type D, available from Whatman, USA). There followed degassing of the assembly in a vacuum. The pulpy mass was poured onto a roughened 6-by-6-centimeter glass substrate, dried for 1 hour at 70 degrees C., and activated for 4 hours at 150 degrees C. in a high vacuum. The resulting layer had a thickness of approximately 2 millimeters. The substrates were stored over phosphorus pentoxide.

The resulting assembly was squeezed down to a thickness of approximately 5 millimeters by application of a 450-gram stamper. The compressed assembly was then incubated for 1 hour at 30 degrees C. Subsequently, the molecular sieve adsorption plate was removed and the adsorption layer thereon immediately sprayed with Enhance®. Autoradiography was then carried out according to the directions given by R. A. Laskey, Radioisotope Detection by Fluorography and Intensifying Screens, Amersham, United Kingdom, Review 23, 1984. The duration of the exposure was 2 days. Scattered Pseudomonas colonies showed up as black spots with a diameter of 5 millimeters. The dominant background of the Alcaligenes colonies remained invisible. Pseudomonas metabolizes tritium-treated glucose to produce $^3H_2O$ but Alcaligenes does not metabolize glucose.

Example 2. The procedure was the same as in Example 1 above, except for the following modifications: Instead of using the $^3H$-glucose, D-[$^{14}C(U)$]-glucose, also available from NEN/DuPont, USA, at 3 curie/mole was used as the radioactive incubating medium. A hydrophobic filter was made by baking a glass-fiber filter, CF/A available from Whatman, USA, with Repel-Silan, available from LKB, Sweden, at 160 degrees C. until dry. The resulting pore size and layer thickness of the hydrophobic filter were 1.4 micrometer and 0.27 millimeter, respectively.

A $CO_2$-specific adsorption medium was made as follows: lime tablets, available from Dräger, Switzerland, were finely ground by mortar and pestle and formed into a paste with water. The paste was spread out with a spatula to form a 2-millimeter layer on a 6-by-6-centimeter glass substrate, and subsequently dried in an desiccator over NaOH tablets for several days. Further processing was as in Example 1.

The glucose-metabolizing Pseudomonas colonies produced $^{14}CO_2$ and showed up as 5-millimeter black spots. The Alcaligenes colonies remained invisible.

Example 3. The procedure was the same as in Example 1 above, with the following modifications: Instead of plate count agar, a carbon-free mineral medium was used, as described by H. Kulla et al., Arch. Microbiol., Vol. 135 (1983), pp. 1–7. A filter membrane of regenerated cellulose, available from Sartorius, Germany, was inoculated directly by spreading of biomass from the aerobic stage of a waste treatment plant. Gaseous xylol formed in an desiccator was used as a source of carbon and of energy. Colonies having a diameter of 1 to 2 millimeters are formed within a week. The radioactive incubating solution included 0.5% molten agar and 5 millimole 2-Cl-5-(methyl-$^3H$)-pyridine at 10 curie/millimole. The hydrophobic filter consisted of a 0.17-millimeter-thick silicone membrane made from Sylgard 18, available from Dow Corning, USA. A supporting fabric consisting of a layer of commercially available medical gauze was placed between the colonies and the silicone membrane. The incubation period was 3 hours. The adsorption medium consisted of a PSC-finished substrate coated with silica gel 60 to a thickness of 2 millimeters without fluorescence indicator, available from Merck, Germany. Otherwise, processing was as in Example 1.

Colonies capable of oxidizing the methyl group in the 2-chloro-5-methyl-pyridine showed up as dark spots, removable from the cellulose support filter by customary microbiological methods.

While the foregoing illustrative examples used discrete microbial colonies grown on a support, which provided the advantage of allowing identification and quantification of the colonies having the metabolic capability being studied, it will be recognized that discrete colonies are not required simply to learn whether microorganisms capable of metabolizing the labeled substances are present in a sample.

I claim:

1. A device for the detection of microorganisms which produce a low-molecular-weight metabolite comprising:
    a semipermeable medium having a pore size in the range from 0.01 to 2 micrometers which is permeable to the low-molecular weight metabolite;
    a support for growing microorganisms thereon and for holding a radioactively labeled substance from which the metabolite can be produced by the microorganisms being detected, the support being positioned at a first side of the semipermeable medium; and
    an adsorption medium positioned at a second side of the semipermeable medium opposite to the first side, the adsorption medium being able to effectively adsorb the metabolite and being transferable for analysis to detect the presence of radioactively labeled metabolite.

2. The device of claim 1, wherein the support comprises a hydrophilic sterile filter membrane.

3. The device of claim 1, wherein the semipermeable medium comprises hydrophobic material having a pore size in the range from 0.02 to 2 micrometers.

4. The device of claim 3, wherein the pore size the hydrophobic material is in the range from 0.02 to 0.2 micrometer.

5. The device of claim 1, wherein the adsorption medium comprises a material selected from the group consisting of a molecular sieve, silica gel, lime, gypsum, and aluminum oxide.

6. The device of claim 1, further comprising a supporting medium interposed between the support and the semipermeable medium.

7. The device of claim 1, wherein the support comprises a filter membrane for growing microorganisms in one or more discrete colonies, and the adsorption medium is in the form of a cohesive layer adjoining to and conformably disposed with the semipermeable medium and the support, the adsorption medium layer being removable from the semipermeable medium and transferable for analysis to detect the presence of radioactively labeled metabolite and to identify specific colonies of microorganisms producing the radioactively labeled metabolite.

* * * * *

UNITED STATES PATENT AND TRADEMARK OFFICE
CERTIFICATE OF CORRECTION

PATENT NO. : 5,348,884
DATED : September 20, 1994
INVENTOR(S) : Hans Kulla

It is certified that error appears in the above-identified patent and that said Letters Patent is hereby corrected as shown below:

Col. 1, line 66, "can" should read -- can be --. Col. 2, line 32, "Thus, for" should read -- Thus, for example, desirable metabolites may include water labeled with --. Col. 5, line 1, "millimose" (both occurrences) should read -- millimole --.

Signed and Sealed this

Third Day of January, 1995

Attest:

BRUCE LEHMAN

Attesting Officer

Commissioner of Patents and Trademarks